US010786579B2

(12) United States Patent
Aggerbeck et al.

(10) Patent No.: US 10,786,579 B2
(45) Date of Patent: Sep. 29, 2020

(54) SKIN TESTING FOR TUBERCULOSIS IN IMMUNOCOMPROMISED PERSONS

(71) Applicant: Statens Serum Institut, København S (DK)

(72) Inventors: Henrik Aggerbeck, Copenhagen (DK); Peter Lawætz Andersen, Brømshøj (DK); Morten Ruhwald, Copenhagen (DK)

(73) Assignee: Statens Serum Institut, København S (DK)

( * ) Notice: Subject to any disclaimer, the term of this patent is extended or adjusted under 35 U.S.C. 154(b) by 0 days.

(21) Appl. No.: 15/775,673

(22) PCT Filed: Nov. 15, 2016

(86) PCT No.: PCT/DK2016/050366
§ 371 (c)(1),
(2) Date: May 11, 2018

(87) PCT Pub. No.: WO2017/084671
PCT Pub. Date: May 26, 2017

(65) Prior Publication Data
US 2019/0151479 A1 May 23, 2019

(30) Foreign Application Priority Data

Nov. 18, 2015 (DK) .............................. 2015 00739
Feb. 1, 2016 (DK) .............................. 2016 00064

(51) Int. Cl.
| A61K 39/04 | (2006.01) |
| A61K 39/02 | (2006.01) |
| G01N 33/554 | (2006.01) |
| A61K 49/00 | (2006.01) |
| A61K 9/00 | (2006.01) |
| A61K 39/09 | (2006.01) |

(52) U.S. Cl.
CPC ........ *A61K 49/0006* (2013.01); *A61K 9/0019* (2013.01); *A61K 39/04* (2013.01); *A61K 39/09* (2013.01)

(58) Field of Classification Search
CPC ......... A61K 39/00; A61K 39/02; A61K 39/04
USPC ............................ 424/9.1, 9.2, 243.1, 248.1
See application file for complete search history.

(56) References Cited

FOREIGN PATENT DOCUMENTS

WO WO 2011/135369 11/2011

OTHER PUBLICATIONS

Ruhwald, Morten, "What are the prospects of an IGRA-skintest"?, 2nd European Advances Course in Clinical Tuberculosis, pp. 1-14, Sep. 22, 2014.*
Bergstedt, W., et al. PLoS ONE, vol. 5, Iss. 6, pp. 1-6, Jun. 2010.*
Aggerbeck et al. "Randomised Clinical Trial Investigating the Specificity of a Novel Skin Test (C-Tb) for Diagnosis of *M. tuberculosis* Infection", Plos One, vol. 8, Issue 5, e64215, 2013.
Aggerbeck et al. "Safety of ESAT-6", Tuberculosis, 86, 363-373, 2006.
Champman et al. "Rapid detection of active and latent *Mycobacterium tuberculosis* infection in HIV-infected Zambians by enumeration of RD1 gene product-specific T cells", Transactions of the Royal Society of Tropical Medicine and Hygiene, 95, 244-249, 2001.
Chapman et al. "Rapid detection of active and latent tuberculosis infection in HIV-positive individuals by enumeration of *Mycobacterium tuberculosis*-specific T cells", AIDS, 16:2285-2293, 2002.
Litvinov et al, AM J Respir Crit Care Med 185; A4703.2012.
Litvinov et al. "Diaskintest—A New Method of Tb Diagnostics", ajrccm-conference.2012.185.1_meetingabstracts.a4703.
Cattamanchi et al. "Interferon-Gamma Release Assays for the Diagnosis of Latent Tuberculosis Infection in HIV-Infected Individuals: A Systematic Review and Meta-Analysis", JAIDS, 56(3) 230-238, 2011.
Hammond et al: "Mycobacterial T cell responses in HIV-infected patients with advanced immunosuppression", Journal of infectious diseases. JID, vol. 197, No. 2, 15, pp. 295-299, Jan. 2008.
Hanif et al: "Species-specific c antigenic *Mycobacterium tuberculosis* proteins tested by delayed-type I hypersensitivity response", Int J Tuberc lung dis, pp. 489-494, Jan. 1, 2010.
Hoff et al. "Sensitivity of C-Tb: a novel RD-1-specific skin test for the diagnosis of tuberculosis infection", Eur REspir J,47:919-928, 2016.
Pankratova L et al. "Experience of using Diaskintest by tuberculosis patients", European Respiratory Journal, vol. 40, suppl 56/P431, 2012.
Sester et al. "Risk assessment of tuberculosis in immunocompromised patients. A TBNET study", AM J Respir Crit Care Med,190(10): 1168-76, 2014.
Weldingh et al. "ESAT-6/CFP10 skin test predicts disease in *M. tuberculosis*—infected guinea pigs", Plos one, vol. 3, No. 4, pp. 1-6, Apr. 23, 2008.
Communication pursuant to Art 94(3) received in EP 16797736 dated Aug. 5, 2019.
Liu et al., "Quantification of circulating *Mycobacterium tuberculosis* antigen peptides allows rapid diagnosis of active disease and treatment monitoring", Apr. 11, 2017, pp. 3969-3974, vol. 114, No. 15, Publisher: PNAS USA.
Slogotskaya et al., "Comparative results of skin testing using tuberculosis allergen recombinant (CFP-10-ESAT-6) and QuantiFERON GIT in children and adolescents with TB", Jan. 1, 2014, p. P2597, vol. 44, Publisher: European Respiratory Journal.

(Continued)

*Primary Examiner* — Rodney P Swartz
(74) *Attorney, Agent, or Firm* — Suzannah K. Sundby, Esq.; Canady + Lortz LLP

(57) ABSTRACT

Disclosed herein is the use of *Mycobacterium tuberculosis* antigens for use in in vivo determination of the presence of Mtb infection in immunocompromised persons or persons co-infected with HIV and the for preparing a diagnostic reagent for skin testing (a skin test reagent) for robust assessment of the presence of Mtb infection infection in an individual wherein the individual is an immunocompromised person or a person co-infected with HIV.

20 Claims, 1 Drawing Sheet

(56) References Cited

OTHER PUBLICATIONS

Figure 1:
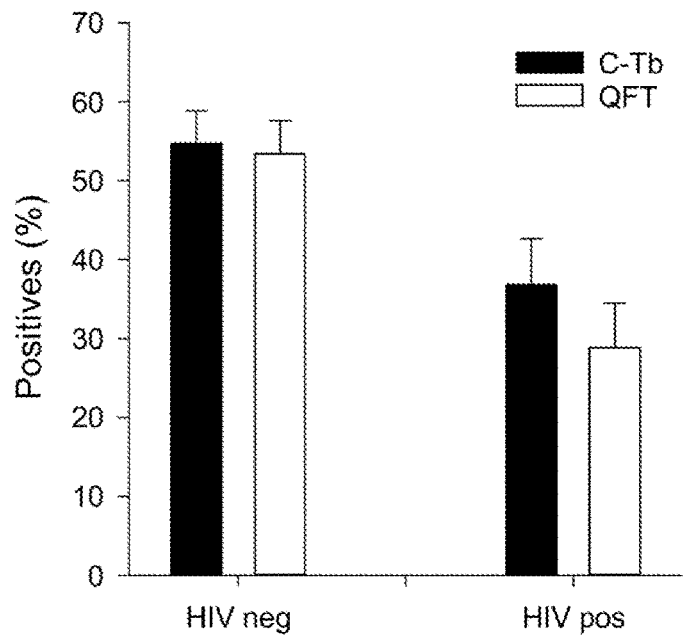
Figure 2:
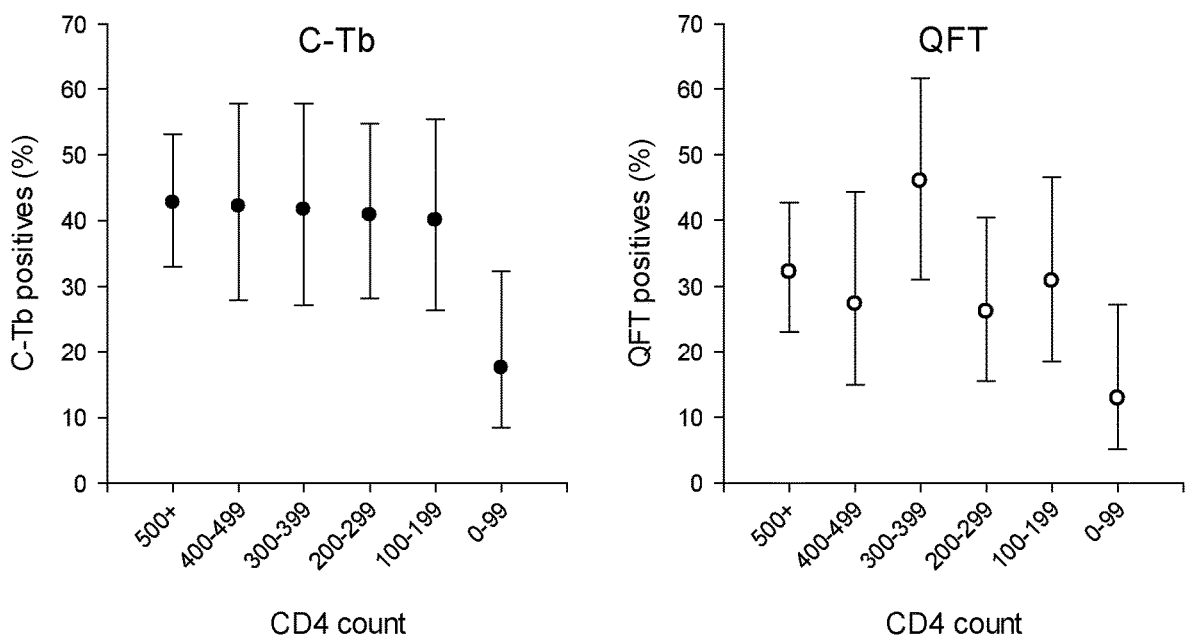

Slogotskaya et al., "New skin test with recombinant protein CFP10-ESAT6 in patients (children and adults) with tuberculosis, non-tuberculosis disease and latent TB infect.", Sep. 1, 2012, p. P416, vol. 40, No. Suppl 56, Publisher: European Respiratory Society.
Tincati et al., "Distinguishing Latent from Active *Mycobacterium tuberculosis* Infection Using Elispot Assays: Looking Beyond Interferon-gamma", May 7, 2012, pp. 89-99, vol. 1, No. 2, Publisher: Cells.
Zheng et al, "Differential MicroRNA Expression in Human Macrophages with *Mycobacterium tuberculosis* Infection of Beijing/W and Non-Beijing/W Strain Types", Jun. 8, 2015, p. e0126018, vol. 10, No. 6, Publisher: PLoS One.

\* cited by examiner

SKIN TESTING FOR TUBERCULOSIS IN IMMUNOCOMPROMISED PERSONS

FIELD OF THE INVENTION

The present invention relates to the use of *Mycobacterium tuberculosis* antigens for preparing a specific skin test composition with improved TB diagnostic performance in *M. tuberculosis* and HIV co-infected persons. The present invention provides a composition comprising *Mycobacterium tuberculosis* (Mtb) antigens for in vivo diagnosis of Mtb infection in immunocompromised persons or persons co-infected with HIV, wherein the reagent comprises a cocktail of the two antigens ESAT6 and CFP-10.

GENERAL BACKGROUND

Overview of TB/PPD

Since its discovery in 1908 by Robert Koch, tuberculin purified protein derivative (PPD) has been in use as a diagnostic test for latent Mtb infection.

Using a diagnostic test for latent Mtb infection to guide preventive treatment, has a dramatic effect on later development of TB disease. Mtb infected people have no symptoms and require a milder treatment regimen, whereas patients with active TB disease have severe disease, high mortality and require longer and more complex treatment. It is believed that ⅓ of the world population is infected with Mtb, 8 million develop active TB each year of whom 1.3 million die.

When applied as a diagnostic test, a small volume of 0.1 mL PPD is injected in the upper layer of the skin and following 2-3 days, a positive reaction can be determined by measuring the induration of the skin using a simple ruler. The immunological background of the PPD skin reaction is a type-IV delayed type hypersensitivity reaction, a reaction mediated primarily by PPD specific Th1 T cells.

PPD when applied as described by Mendel and Mantoux, has been endorsed by the World Health Organization since 1955, and the PPD based Tuberculin Skin Test (TST) remains one of the most widely used diagnostic tests with more than 50 million tests performed each year.

PPD is a complex culture filtrate from *M. tuberculosis* comprising more than 1000 protein antigens in addition to lipids and carbohydrates. This makes PPD broadly recognized by Mtb infected individuals and it is very immunogenic driving a strong Th1 T cell response in the skin. However, the crude and complex composition of PPD is also the cause of the problems with the PPD TST. Importantly, the multiple antigens in PPD are also recognized by regulatory T cells, CD1 restricted T cells and Th2 cells, which selectively can inhibit the type-IV reaction from occurring. Furthermore, multiple antigens in PPD are also expressed by environmental mycobacteria and the *Bacillus* Calmette-Guerin (BCG) used for vaccination against TB, rendering the PPD test unspecific.

HIV and Immunocompromised Individuals.

Another major challenge to the use of PPD TST is its unreliability in immunocompromised persons. Especially in Human Immunodeficiency Virus (HIV) infected persons, the PPD TST frequently becomes unresponsive and false negative, or it may turn out false positive due to the application of a too low cut off.

The immunological background of HIV's impact on the ability of PPD to generate the type-IV skin reaction is complex, however it is established that the selective loss of CD4 T cells by the HIV infection is the root cause. Therefore, the immunodeficiency caused by the loss of CD4 T cells is both the underlying factor leading to disease from opportunistic infectious virus and bacteria (the hallmark of HIV/AIDS), as well as the inability to react to PPD TST.

The consequence of this dilemma can be deadly. Often HIV infection (or other immunodeficiency) is not diagnosed at time of PPD TST testing. Wherefore, the responsible physician often has a false reliance of the PPD TST result. This false sense of security frequently leads to misdiagnosis and absence of adequate treatment of Mtb infection, leading to later development of active TB disease. In fact, Mtb infected patients with HIV/AIDS have a 10% annual risk of developing TB, and TB is the disease that kills most HIV/AIDS patients.

Tackling the Challenge of Cross Reactivity to BCG

As mentioned above the cross reactivity to BCG and environmental mycobacteria is a major limitation to PPD TST. Cross reactivity compromises specificity and potentially leads to overtreatment due to false positive responses. The specificity issue can be addressed to some extent—but not completely—by increasing the cut off for the TST from 5 mm to 10 mm or even 15 mm induration, however increasing the cut off compromises the sensitivity of the test.

Especially for HIV infected and other large patient groups at highest risk of developing TB if not adequately offered treatment for Mtb infection, a further loss of sensitivity can prove fatal. Therefore, HIV testing before PPD TST testing in e.g. BCG vaccinated would be required for optimal performance of the PPD TST. However, due to limited resources and taboo both among health care providers and patients, HIV testing is often not offered to or accepted by the person in need of PPD TST testing.

The Era of Specific Testing

The discovery of Mtb specific immunodominant antigens has led to a significant new avenue for the diagnosis of infection with Mtb. Early work had shown the potential to replace PPD TST by a test that assayed the in vitro production of interferon gamma (IFN-γ) by T cells in response to Mtb antigens. Around the same time, a major advance was the discovery of the highly immunogenic antigens, early secreted antigenic target 6 (ESAT-6) and culture filtrate protein 10 (CFP-10) that improved specificity significantly. These antigens are encoded within the region of difference 1 (RD1) of the pathogen and are consequently absent from all Bacille Calmette Guerin (BCG) vaccine strains and most non-tuberculous mycobacteria (exceptions include *Mycobacterium kansasii, Mycobacterium marinum, Mycobacterium szulgai*).

IFN-γ responses to overlapping peptides of the RD1 encoded antigens ESAT-6 and CFP-10 form the basis for the detection of Mtb infection in two commercially available IFN-γ release assays (IGRA) tests: QuantiFERON-TB Gold (QIAGEN, Germany) and T-SPOT.TB (Oxford Immunotec, Oxford, UK).

QuantiFERON-TB Gold (QFT, QIAGEN, Germany), a whole blood enzyme-linked immunoassay (ELISA) has European CE mark approval and American Food and Drug Administration (FDA) approval for the detection of both latent TB infection and disease.

T-SPOT.TB (Oxford Immunotec, Oxford, UK), an enzyme-linked immunospot assay (ELISPOT) that uses peripheral blood mononuclear cells has European CE mark approval and FDA approval.

Limitations of IGRA However, despite obvious superior specify of IGRA compared to the TST, IGRA have several limitations:

The blood sample based IGRA tests require blood draw, complex laboratory equipment and trained staff to perform it. These constraints render the test almost impossible to implement in the resource restraint settings where such tests are in highest demand. IGRA tests are also subject to problems in the pre-analytical step, e.g. false negative responses due to delayed initiation of the incubation step.

Vis-à-vis the PPD TST, the diagnostic performance of the IGRA tests also requires that the person subjected for testing can mount a reliable immune response. Just as for the PPD TST the sensitivity of the IGRA may be impaired in immunosuppressed individuals. In particular, patients with HIV infection and low CD4 T cell counts or patients receiving immunosuppressing medication frequently experience false negative or indeterminate responses.

The probable underlying cause of the poor performance of the IGRA tests in immunosuppressed, are their reliance on the detection of a very weak IFN-γ signal to be deemed positive (17.5 pg/ml or 6 reactive T cells per 200.000 PBMCs). Such low responses are bordering the detection levels of the most sensitive assays used in clinical medicine.

Therefore, a skin test wherein the immune reaction can be driven by potentially any specific T cell available in the body, appears per se much more robust compared to an in vitro diagnostic test in which the available number of T cells is confined to the small number of cells comprised in the sample.

In a meta analysis Cattamanchi and colleagues (JAIDS 2011, 56(3) 230-238) showed that for HIV-infected persons with active TB (a surrogate reference standard for LTBI), pooled sensitivity estimates were heterogeneous but higher for T-SPOT.TB assay (72%; 95% CI, 62 to 81%) than for QFT assay (61%; 95% CI, 47 to 75%) in low- and middle income countries. However, neither IGRA was consistently more sensitive than the PPD TST in head-to-head comparisons. The authors concluded that IGRAs, may be less affected by the degree of HIV induced immunosuppression compared to PPD TST, but results differed across geographical settings.

The potentially life-threatening consequences of false negative PPD TST and IGRA results was described by Sester et al (Am J Respir Crit Care Med. 2014 Nov. 15; 190(10):1168-76. doi: 10.1164/rccm.201405-0967OC). In this large prospective study including 768 patients with HIV infection, eight patients with HIV-infection developed active TB disease during follow-up. Five of the 8 patients with a determinate IGRA test-result had a false negative IGRA test-result at the time of screening and were not offered preventive treatment. An additional 3 HIV infected who developed TB, had an indeterminate IGRA test result. PPD TST was done on all 11 who developed TB. In this group only 4 of 11 tested were positive using an HIV optimized cut off at 5 mm.

Diaskintest is a recombinant fusion protein of CFP-10-ESAT6 produced in *E. coli* BL21 (DE3)/pCF-ESAT. The protein is expressed as a 6× histidine-tagged protein and is manufactured by Generium in the Russian federation. The dose is 0.2 µg/0.1 mL. Any size of induration is considered indicative of Mtb infection. The histidine tag poses a risk of neo-epitopes. Diaskintest is reported to perform with acceptable specificity but with high rate (4-14%) vesicular necrotic changes, lymphangitis, and lymphadenitis (Kiselev, V I; Probl. Tuberk. Bolezn. Legk. 2009; 2:11-6). Repeated injections of high doses of antigen may pose a risk of sensitization, which may lead to false-positive reactions further driving the risk of adverse reactions. Diaskintest is the only product in clinical use. Several studies have explored Diaskintest performance in HIV infected individuals and found a very strong negative impact of HIV infection on Diaskintest performance. Pankratkova found 42.9% sensitivity among HIV-positive subjects, compared to 79.7% in subjects without HIV infection (Pankratova L et al European Respiratory Journal 2012, vol 40, Suppl 56/P431), similar significant findings were reported by Litvinov; 43.5% in HIV infected compared to 89.7% in HIV-negative cases (Litvinov et al, Am J Respir Crit Care Med 185; 2012: A4703).

In summary the PPD TST is an attractive and simple test for latent Mtb infection, however the PPD antigen component is unspecific and PPD TST test results in HIV infected are frequently false negative. The IGRA test is based on the specific Mtb antigens ESAT-6 and CFP-10, and have addressed the specificity issues of the PPD TST test, however these tests are complex to implement and perform, and also frequently present with false negative in HIV infected people. Diaskintest provides a skin test with IGRA like specificity, however the performance of Diaskintest in HIV infected is severely affected, with sensitivity reduced to half in HIV infected compared to HIV-non-infected. Therefore, there is a need for a new diagnostic skin test for Mtb infection with superior specificity to PPD TST and improved sensitivity in HIV infected.

SUMMARY OF THE INVENTION

The invention discloses an in vivo diagnostic method (skin testing) and diagnostic agents for diagnosing Mtb in immunocompromised individuals or individuals who are co-infected with HIV, individuals who would else not be recognized as being infected with *M. tuberculosis* due to lack of sensitivity of existing tests.

The effect is achieved by using a cocktail of the *M. tuberculosis* antigens ESAT6 and CFP-10 for preparing a skin test agent composed of a cocktail comprising these antigens. In a preferred embodiment a cocktail of the antigens recombinant ESAT-6 (rdESAT-6) and recombinant CFP-10 (rCFP-10) are used. The C-Tb antigen cocktail performs very robust in HIV infected, demonstrating only 33% reduction in sensitivity overall compared to 45% for Quantiferon. In contrast to other test modalities, C-Tb seems only affected by HIV infection in the most severe cases with CD4+ T cell count<100 CD4+ T cells/μl.

DETAILED DISCLOSURE OF THE INVENTION

The present invention discloses a composition comprising *Mycobacterium tuberculosis* antigens for use in in vivo determination of the presence of Mtb infection in immunocompromised persons or persons co-infected with HIV, wherein the agent comprises a cocktail of the two antigens ESAT6 and CFP-10.

The present invention discloses the use of *Mycobacterium tuberculosis* antigens for preparing a diagnostic agent for skin testing (a skin test agent) for robust assessment of the presence of Mtb infection in an individual wherein the individual is an immunocompromised person or a person co-infected with HIV.

The present invention also discloses a method for diagnosing Mtb infection in immunocompromised persons or in persons co-infected with HIV. The diagnostic method is based on measuring the magnitude of a reaction in the skin generated in response to stimulation of specific immune cells by injecting a small volume of Mtb specific antigens.

The two antigens are preferably cloned, produced and purified from a suitable organism e.g. from *Lactococcus lactis*, rESAT6 and rCFP-10, and most preferably a double-ESAT-6 (rdESAT-6; two ESAT-6 molecules fused together). rdESAT-6 and rCFP-10 are preferably mixed in a 1:1 (w/w) ratio. The composition comprises the two antigens mixed in a vehicle where the most preferred vehicle comprises phosphate buffered saline (PBS) with 0.01% Polysorbate20 and 0.5% phenol.

Definitions

The term "Tuberculosis" refers to the clinical condition Tuberculosis disease, caused by various strains of mycobacteria, usually *Mycobacterium tuberculosis*.

The term "latent *M. tuberculosis* infection" refers to subclinical or latent infection with *M. tuberculosis*, which is defined by the presences of an immune response to *M. tuberculosis* without signs or symptoms of active disease.

The term "ESAT-6" in the present invention refers to the 6 kDa early secretory antigenic target produced by *Mycobacterium tuberculosis* (esxA), is a secretory protein and potent T cell antigen, locus tag Rv3875

The terms "CFP-10" in the present invention refers to the 10 kDa secreted antigen from *Mycobacterium tuberculosis* also known as ESAT-6-like protein esxB or secreted antigenic protein MTSA-10 or 10 kDa culture filtrate antigen, Rv3874.

The terms "cocktail" and "antigen cocktail" in the present invention refers to at least two proteins together in vehicle or solution.

The term "immunodeficiency" or "immunosuppression" or "immunocompromised" refers to a state in which the immune system's ability to fight infectious disease or mount an immune response is compromised or entirely absent.

The term "C-Tb" refers to the preparation of a composition of rdESAT-6 and rCFP-10.

The term "HIV" refers to the lentivirus Human Immunodeficiency Virus, that causes HIV infection and over time can lead to acquired immunodeficiency syndrome (AIDS)

By the term "fusion protein" is understood a random order of two or more immunogenic polypeptides from *M. tuberculosis* or analogues thereof fused together with or without an amino acid linker/spacer(s) of arbitrary length and sequence. To avoid protein aggregation in the down-stream production all cysteines in the fusion protein can be replaced with any amino acid but serine is the preferred substitute because of its high structural similarity with cysteine.

The surprising improved diagnostic sensitivity in HIV infected is likely achieved through a summary of mechanisms. The C-Tb skin test reagent is composed of a cocktail of antigens, compared to e.g. the Diaskintest which is a hybrid-construct comprising two protein joined by a linker. The cocktail design of C-Tb offers several potential benefits including better exposure of epitopes without interference from linker proteins. In addition, the skin test format offers advantages over the IGRA format. The protracted incubation period allows recruitment of the same population of effector T cells as monitored in the IGRA but further also recruitment of a population of less differentiated cells. The broader T cell recruitment combined with the skin test cocktail format likely allowed for the superior sensitivity.

The diagnostic agent for the skin test comprises the two antigens ESAT6 and CFP-10. In a preferred embodiment the skin test reagent is composed of a cocktail of recombinant versions of the two antigens. In the most preferred embodiment the two antigens are double-ESAT-6 (rdESAT-6; two ESAT-6 molecules fused together) and rCFP-10. The two antigens are cloned, fermented and purified in a suitable organism e.g. from *Lactococcus lactis* or *E. coli*. The antigens are mixed in a vehicle or pharmaceutical acceptable carrier. In a most preferred embodiment rdESAT-6 and CFP-10 are mixed in a 1:1 (w/w) ratio in a vehicle of phosphate buffered saline (PBS) with 0.01% Polysorbate 20® (and 0.5% phenol). The amount of antigen dose is in the range of 0.25-2.0 µg/mL of each antigen. The preferable amount is 0.1 µg/0.1 mL corresponding to a total concentration of 1 µg antigens/mL corresponding to 0.5 µg/ml of each. This specific preparation of rdESAT-6 and rCFP-10 is termed C-Tb. The reagent is not restricted to these antigens alone but may in addition include other antigens like Rv3615.

Performing the Skin Test

Skin testing is done by injecting a small volume of C-Tb intradermally, e.g. 0.1 ml into the inner surface of the forearm.

The injection should be made with a tuberculin syringe, with the needle bevel facing upward. However, other means of intradermal injection can also be used. When placed correctly, the C-Tb injection should produce a pale elevation of the skin (a wheal) 6 to 10 mm in diameter.

The skin test reaction should be read between 48 and 72 hours after administration. A patient who does not return within 72 hours will need to be rescheduled for another skin test.

The magnitude of the skin reaction may be detected by measuring the induration in millimeters (diameter of palpable, raised, hardened area or swelling). The diameter of the indurated area should be measured across the forearm (perpendicular to the long axis of the forearm).

An induration of 5 millimeters or more as used in the example material is a preferred cut off, non withstanding the fact that other cut offs including 10, 4, 3, 2, 1, or even any reaction above 0 millimeter could be used.

The concept of C-Tb is to combine the well-known Mantoux technique using the specific antigens from IGRAs into a specific skin test using a single universal cut-off of 5 mm induration irrespective of BCG vaccination and HIV status read after 2-3 days to identify Mtb infected individuals delivered and interpreted by point-of-care medical or nursing staff Diagnosis Skin testing with a specific reagent is particularly beneficial for use in persons with immunosuppression. HIV constitutes a key at-risk population wherein Mtb infection rapidly can progress to active disease. HIV infected individuals have a compromised CD4 T cell function, wherefore skin testing with a reagent that specifically targets Th1 T cells and not also Th2 or regulatory T cells could prove superior.

The target population for C-Tb includes individuals exposed to Mtb or individuals showing signs or symptoms of TB with special attention to groups with an increased risk of developing TB once infected. These groups include but are not limited to newly infected cases identified during contact tracing, children below 5 years of age and HIV infected.

The present invention provides a skin test reagent for robust assessment of the presence of Mtb infection in persons co-infected with HIV. As clearly demonstrated in the provided examples, an example of a specific skin test (C-Tb) has superior performance to both PPD TST and IGRA.

rdESAT-6 and CFP-10 are mixed in a (w/w) ratio in a vehicle, although in the preferred embodiment the ratio is 1:1 other w/w ratios including 1:5, 1:4, 1:3, 1:2; 2:1, 3:1, 4:1, 5:1 and other ratios spanning 1:20 and 20:1 would be expected useful.

The amount of antigen dose is in the range of 0.25-20.0 µg/mL of each antigen. A preferable amount is 0.1 µg/0.1 mL corresponding to a total concentration of 1 µg antigens/mL corresponding to 0.5 µg/ml of each. Larger amounts of antigen are expected to drive stronger skin induration responses but increase the risk of adverse or unnecessarily strong reactions. Depending on the clinical setting, genetic or ethnic makeup, degree of immunosuppression or other characteristic of the tested population, the antigen dose can be selected within the range of 0.25-20.0 0.25-20.0 μg/mL of each antigen.

Although the present invention describes the specific preparation of rdESAT-6 and rCFP-10, the agent is not restricted to these antigens alone but may in addition include other antigens like espC (Rv3615) or other specific antigens expressed by *M. tuberculosis*. Several antigens known to be specifically expressed by infectious organisms in the *M. tuberculosis* complex could be suitable additions or substitutes to ESAT-6 and CFP-10 in C-Tb. These antigens include RD1 restricted antigens, RD1 associated antigens and antigens with immunodiagnostic potential such as Rv2564, Rv3865, Rv3877, Rv2348, Rv3614, Rv3616 and other known to the skilled addressee.

The preferred embodiment of C-Tb test teaches intradermal injection. It should be understood that injection using syringe and needle is only one of several methods of administration. Alternative methods include the Heaf gun (sterneedle) and various other methods such as but not limited to jet injection, projectile delivery using powder and gold particles (i.e., gene gun), solid microneedle patches (metal or dissolving microneedles), topical addition of C-Tb after microneedle pretreatment, tattoo guns, or technologies designed to increase skin permeability in combination with a delivery patch e.g. skin abrasion, ultrasound, electroporation, laserproration, chemical enhancers, and thermal ablation.

FIGURE LEGENDS

FIG. 1. Positivity rate of C-Tb (black; cut-off 5 mm) and QFT (white; cut-off 0.35 IU/mL) among 534 HIV negative and 277 HIV positive TB suspects. Error bar indicate 95% CI.

FIG. 2. Positivity rate of C-Tb (black) and QFT (white) stratified according to CD4 count among 292 TB suspects. Error bar indicate 95% CI.

EXAMPLES

The diagnostic agent C-Tb was prepared by cloning, fermenting and purifying recombinant versions of the two antigens rdESAT-6 and rCFP-10 from *Lactococcus lactis*. The antigens were mixed in equimolar amounts of ESAT-6 and CFP-10 corresponding to a 1:1 w/w ratio of rdESAT-6 and rCFP-10 in a vehicle of phosphate buffered saline (PBS) with 0.01% Polysorbate 20® (and 0.5% phenol)

The diagnostic performance of C-Tb, PPD and an IGRA named QuantiFERON®-TB Gold In Tube (QFT) were compared in a phase III trial in infants and children less than 5 years of age with suspected Mtb infection, and in older children and adults with suspected TB disease. The trial of 1190 participant included 299 HIV positives and 730 HIV negatives. Blood for QFT testing was collected prior to skin testing. C—Tb and PPD were injected double blind into separate arms in a randomized, split body design. Results from the volunteers with paired results available were included.

As evident from FIG. 1, C—Tb and QFT showed the same positivity rate among HIV negatives, 292/534 (54.7%) were positive with C-Tb and 285/534 (53.4%) were positive with QFT. A total of 277 HIV infected individuals were tested with both tests. Surprisingly C-Tb disclosed significantly more Mtb infected than the QFT test, 102/277 (36.8%) tested positive with C-Tb and only 80/277 (28.9%) tested positive with QFT, (table 1, McNemar; P=0.009).

TABLE 1

| | | QFT | | |
|---|---|---|---|---|
| | HIV pos | + | − | S |
| C-Tb | + | 59 | 43 | 102 |
| | − | 21 | 154 | 175 |
| | S | 80 | 197 | 277 |

P = 0.009

When stratifying rest results by CD4 T cell count (FIG. 2), it becomes evident that the higher sensitivity by C-Tb stems from a significantly increased robustness not only in the low CD4 T cell strata but across the whole spectrum of CD4 T cell counts.

The invention claimed is:

1. A method of eliciting an immune response in an immunocompromised subject having a latent *M. tuberculosis* (Mtb) infection and showing no symptoms characteristic of an active Mtb infection which comprises administering intradermally to the immunocompromised subject a cocktail comprising an ESAT6 Mtb antigen and a CFP-10 Mtb antigen.

2. The method according to claim 1, which further comprises measuring a diameter of any induration resulting from the administration to measure the magnitude of the immune response.

3. The method according to claim 1, wherein the ESAT6 Mtb antigen or both the ESAT6 Mtb and CFP-10 antigens are cloned, produced, and purified from *Lactococcus lactis*.

4. The method according to claim 1, wherein the cocktail further comprises a pharmaceutically acceptable carrier.

5. The method according to claim 1, wherein the cocktail further comprises phosphate buffered saline (PBS) with 0.01% polyoxyethylene (20) sorbitan monolaurate and 0.5% phenol.

6. The method according to claim 1, wherein the cocktail comprises recombinant double-ESAT6 Mtb antigen and recombinant CFP-10 Mtb antigen.

7. The method according to claim 6, wherein the recombinant double-ESAT6 and recombinant CFP-10 are present in a 1:1 (w/w) ratio.

8. The method according to claim 6, wherein the recombinant double-ESAT6 and recombinant CFP-10 are present in a ratio between 1:20 (w/w) and 20:1 (w/w).

9. The method according to claim 1, wherein the cocktail comprises a total amount of Mtb antigens ESAT6 antigen and CFP-10 Mtb antigen of an amount of 0.25-2.0 μg/mL of the Mtb antigens ESAT6 antigen and CFP-10 Mtb antigen.

10. The method according to claim 2, wherein the diameter of the induration is measured between 48-72 hours after administration of said cocktail.

11. The method according to claim 1, wherein the cocktail further comprises one or more Mtb antigens in addition to the ESAT6 and CFP-10 Mtb antigens.

12. The method according to claim 11, wherein the one or more Mtb antigens are selected from the group consisting of RD1 restricted antigens, RD1 associated antigens, Rv2564, Rv3865, Rv3877, Rv2348, Rv3614, Rv3615, and Rv3616.

13. The method according to claim 1, wherein the immunocompromised subject is a child.

14. The method according to claim 1, wherein the immunocompromised subject is an adult.

15. The method according to claim 1, wherein the immunocompromised subject is infected with HIV.

16. The method according to claim 1, wherein the immunocompromised subject is suspected of having an Mtb infection.

17. The method according to claim 1, wherein the immunocompromised subject is suspected of having TB disease.

18. A method of performing a skin test on an immunocompromised subject showing no symptoms characteristic of an active Mtb infection which comprises administering intradermally to the immunocompromised subject a cocktail of Mtb antigens, said Mtb antigens consisting of an ESAT6 Mtb antigen and a CFP-10 Mtb antigen, and detecting any skin reaction by measuring a diameter of any induration resulting from the cocktail of Mtb antigens.

19. The method according to claim 18, wherein the immunocompromised subject is infected with HIV.

20. The method according to claim 18, wherein the immunocompromised subject is suspected of having an Mtb infection.

* * * * *